(12) United States Patent
O'Toole

(10) Patent No.: US 6,379,312 B2
(45) Date of Patent: Apr. 30, 2002

(54) END TIDAL CARBON DIOXIDE SAMPLING DEVICE

(76) Inventor: James O'Toole, 10040 Graylock Way, Knoxville, TN (US) 37931

( * ) Notice: Subject to any disclaimer, the term of this patent is extended or adjusted under 35 U.S.C. 154(b) by 0 days.

(21) Appl. No.: 09/748,154

(22) Filed: Dec. 27, 2000

Related U.S. Application Data

(60) Provisional application No. 60/173,294, filed on Dec. 28, 1999.

(51) Int. Cl.[7] .................................................. A61B 5/08
(52) U.S. Cl. ....................................... 600/529; 600/532
(58) Field of Search ................................ 600/529, 532; 128/207.18

(56) References Cited

U.S. PATENT DOCUMENTS

| | | | |
|---|---|---|---|
| 3,395,701 A | * | 8/1968 | Bartlett et al. ............... 600/532 |
| 4,367,735 A | * | 1/1983 | Dali ....................... 128/207.18 |
| 5,005,571 A | | 4/1991 | Dietz |
| 5,046,491 A | * | 9/1991 | Derrick ................. 128/200.24 |
| 5,335,656 A | | 8/1994 | Bowe et al. |
| 5,335,659 A | * | 8/1994 | Pologe ........................ 600/473 |
| 5,513,634 A | | 5/1996 | Jackson |
| 5,555,890 A | | 9/1996 | Schaller |
| 5,558,090 A | | 9/1996 | James |
| 5,752,511 A | * | 5/1998 | Simmons et al. ...... 128/207.18 |
| 5,937,858 A | | 8/1999 | Connell |

FOREIGN PATENT DOCUMENTS

| | | | |
|---|---|---|---|
| EP | 3 343 821 A2 | 11/1989 | |
| EP | 0933094 A2 | * 4/1999 | .......... A61M/16/06 |

* cited by examiner

Primary Examiner—Robert L. Nasser
Assistant Examiner—Patricia C. Mallari
(74) Attorney, Agent, or Firm—Richard C. Litman

(57) ABSTRACT

An end tidal carbon dioxide addition device coupling to a nasal cannula used on patients under general anesthesia or sedated, to continuously measure the carbon dioxide content of the expired breath. A first embodiment device has a body a pair of nasal ducts with clips to attach to a nasal cannula. A pair of oral ducts collects exhaled oral gases which are combined with the nasal gasses to be analyzed for tidal carbon dioxide content. A pair of posts adjacent the oral ducts stabilize the device on a sedated patient. A second embodiment integrates a nasal cannula with the body to provide an economical disposable device and substitutes a flattened region with an array of apertures for the oral ducts.

8 Claims, 3 Drawing Sheets

END TIDAL CARBON DIOXIDE SAMPLING DEVICE

CROSS-REFERENCE TO RELATED APPLICATION

This application claims the benefit of U.S. Provisional patent application Ser. No. 60/173,294, filed Dec. 28, 1999.

BACKGROUND OF THE INVENTION

1. Field of the Invention

The present invention relates generally to respiratory gas measuring devices and, more specifically, to a disposable device which attaches to a conventional nasal cannulae that fits into the patient's mouth to collect and measure the carbon dioxide content of the expired breath from both expiration sources. In the alternative, the cannulae and the mouth expiration collector are combined as an integrated unit.

2. Description of Related Art

The relevant art of interest describes various cannulae and end tidal sampler devices, but none discloses the present invention, which is a removable addition to a cannulae or a combination cannulae and mouth respiration collector for carbon dioxide analysis.

The relevant art will be discussed in the perceived order of relevance to the present invention.

U.S. Pat. No. 5,046,491 issued on Sep. 10, 1991, to Steven J. Derrick describes an apparatus and method for respired gas collection and analysis. In FIG. 1, a nasal cannulae is inserted in the nares of the nose to collect respired gas which flows into a connecting stem into an apertured oral respired gas capture gas hood. FIG. 2 shows no contact between the oral gas capture assembly and little or no contact between the nasal gas cannula and the nares. The embodiment shown in FIG. 4 requires a corrugated stem connecting the cannulae to the perforated oral gas capture cylinder. The collected nasal and oral gases are conducted separately to a distribution and valve assembly which permits discharge of either nasal gas or oral gas separately, or mixed together for analysis by infrared spectrometry, mass spectrometry, which data may further be converted by analog means to a graph or a digital read-out. The apparatus is distinguishable for its required perforated oral gas capture member and the perforated nasal respired gas cannula member.

U.S. Pat. No. 5,005,571 issued on Apr. 9, 1991, to Henry G. Dietz describes a mouth and nose mask for use with an inhalation therapy and/or breathing monitoring apparatus. The mask has no connections to the inhalation therapy and breathing monitoring apparatus, and is worn over the nasal cannulae. The mask provides for diversion of some of the oral and of the nasal treatment gases in case one passageway is blocked. The system utilizes an optoelectronic sensor and a solenoid valve instead of a mechanical device to indicate the need for the inhalant. The system is distinguishable for its requirement for an optoelectronic sensor and a mask.

U.S. Pat. No. 5,513,634 issued on May 7, 1996, to Frank W. Jackson describes a combined and integral plastic endoscopic bite block airway and nasal cannula device. A cannula is supplied oxygen from a tube and is attached to an open mask having a bite block. The device is distinguishable for its bite block structure.

U.S. Pat. No. 5,335,656 issued on Aug. 9, 1994, to Edwin A. Bowe et al. describes a method and a nasal cannulae for inhalation of a treating gas and sampling of exhaled gas for quantitative analysis from separate nostrils. The cannulae must include a wall member to separate the inhaled and exhaled gases. The device is distinguishable for its required septum in the cannulae.

U.S. Pat. No. 3,395,701 issued on Aug. 6, 1968, to Roscoe G. Bartlett, Jr. et al. describes an end tidal sampler for an oxygen breathing mask. The multi-chambered device is inserted, inside an oxygen mask and includes a hypoxia sensor. A diaphragm is exposed to the mask's interior and another diaphragm exposed to the ambient atmosphere. One-way valves connect the chambers to cause atmospheric pressure acting on one diaphragm upon inspiration to force the end tidal of the previous expiration into the chamber containing the hypoxia sensor. Upon expiration, the expired breath acting upon the second of the diaphragms forces the end tidal sample from the chamber containing the hypoxia sensor. The device is distinguishable for its multi-chambered, one-way valves and required hypoxia sensor.

U.S. Pat. No. 5,555,890 issued on Sep. 17, 1996, to Douglas A. Schaller describes a pharyngeal end-tidal carbon dioxide measuring catheter. An end tidal gas is defined as the last third portion of an exhaled gas mixture which is monitored by a capnometer to measure the concentration of carbon dioxide exhaled by the patient. The 2.5 mm. in diameter tubing has gas intake ports in the end inserted into the oropharynx of the patient through the nasal cavity. A suction trap is inserted in the catheter line leading to the capnograph which measures the carbon dioxide in the end tidal gas. The pharyngeal catheter device is distinguishable for its limitation to nasal gas measurement.

U.S. Pat. No. 5,558,090 issued on Sep. 24, 1996, to Lonnie A. James describes a multi-purpose head-mounted adjustable endotrachial tube holder comprising a cushioned brow band and head band. A brow band extension supports an endotrachial tube holder which has a detachable bite block for the mouth. The device is distinguishable for its singular purpose structure for the mouth.

U.S. Pat. No. 5,937,858 issued on Aug. 17, 1999, to Donald G. Connell describes an oral or nasopharyngeal airway device for administering and sampling inhalant and expired gases. Oxygen is delivered through a tube and an expired gas is removed from a tube. The two tubes are enclosed in another tube for the airway device made of either latex, silicone rubber or soft polyvinylidine fluoride 6 –8 inches long with an outside diameter of one inch to reach the posterior pharynx region. The airway device is distinguishable for its unified structure and limitation for entry to either the mouth or nasal region.

European Patent Application No. 0 343 821 A2, published on Nov. 29, 1989, for George M. Nowak describes a nasogastric tube holding device. A spunlaced polyester pad with adhesive pad wings has a pair of clamping jaws for holding a nasogastric tube. The device is distinguishable for its structure requiring clamping jaws.

None of the above inventions and patents, taken either singly or in combination, is seen to describe the instant invention as claimed.

SUMMARY OF THE INVENTION

The invention is a device that attaches to a nasal cannula having intake ducts for the patient's mouth and nose, to collect and measure the carbon dioxide content of the expired breath. In the alternative, the mouth expired gas is collected by an apertured flattened region of the device rather than by ducts.

Accordingly, it is a principal object of the invention to provide an attachment device to an oxygen delivering cannula for enabling the sampling of the carbon dioxide content of a patient's expired air from both the nose and the mouth.

It is another object of the invention to provide an integrated combination nasal cannula and mouth cannula having intake ducts for monitoring the carbon dioxide content of a patient's expired air.

It is a further object of the invention to provide a carbon dioxide content analyzing device which will collect the expired nasal air by intake ducts and collect expired oral air by a flat apertured intake portion from patients who are either under general anesthesia or under local anesthesia and sedation.

Still another object of the invention is to provide a carbon dioxide content analysis aiding device useful for patients under general anesthesia or sedation which is economical and disposable after use.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to an end tidal carbon dioxide addition device coupling to or integral with a nasal cannulae used on patients under general anesthesia or sedated to measure the carbon dioxide content of the expired breath continuously.

Figure 1:
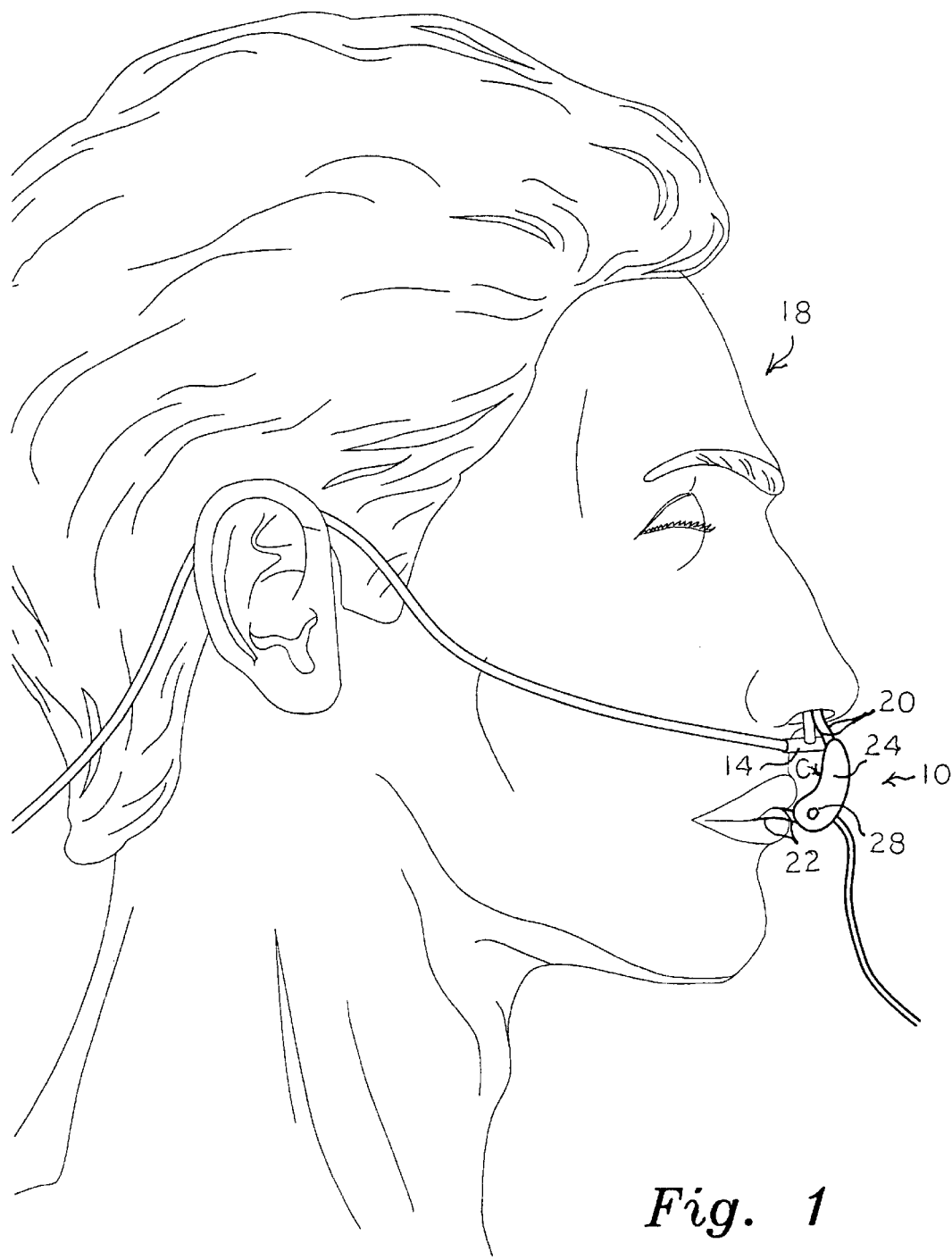
FIG. 1 is an environmental, perspective view of a first embodiment of an end tidal carbon dioxide sampling device attached to a nasal cannula and positioned on a patient according to the present invention.

In FIG. 1, the attachment device 10 of the first embodiment for measuring exhaled end tidal carbon dioxide is attached by a pair of resilient clips 12 (FIG. 2) to a conventional cannula 14 inserted in the nose 16 of an anesthetized or sleeping patient 18, to supply the nasal passages with air or oxygen. A pair of nasal tubes 20 extending approximately a centimeter collect the expired nasal air. A pair of oral tubes 22, each with a larger diameter and longer length, e.g., 1.5 cm., collect the expired oral gases. The tubes 20, 22 are housed in a body 24 which has a critical curvature C to conform to the facial structure of the patient 18. In the alternative, the oral tube 22 can be a singular tube and flattened in cross-section.

Figure 2:
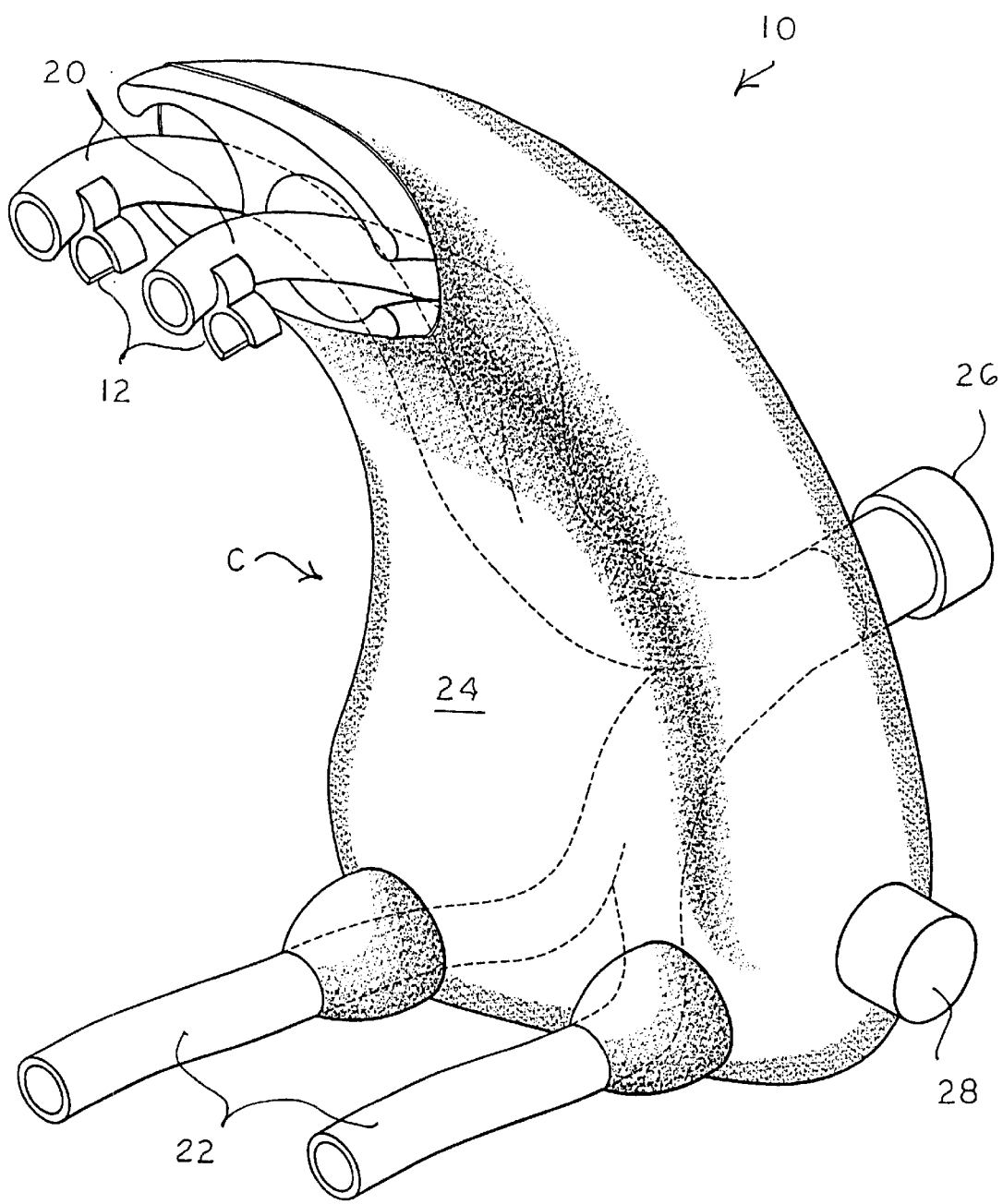
FIG. 2 is an enlarged scale, perspective view of the FIG. 1 carbon dioxide sampling device.

In FIG. 2, an enlarged view of the device 10 is depicted to show the nasal tubes 20 and the oral tubes 22 joining to form a common outlet duct 26 which will be connected to a conduit going to the end tidal carbon dioxide analyzer machine (not shown). A pair of oppositely extending extension posts 28 (one hidden) are provided proximate the bottom of the device 10 for either abutting the mouth or placing inside the mouth of the patient 18 for the purpose of stabilizing the device 10 without resorting to adhesive tape.

Figure 3:
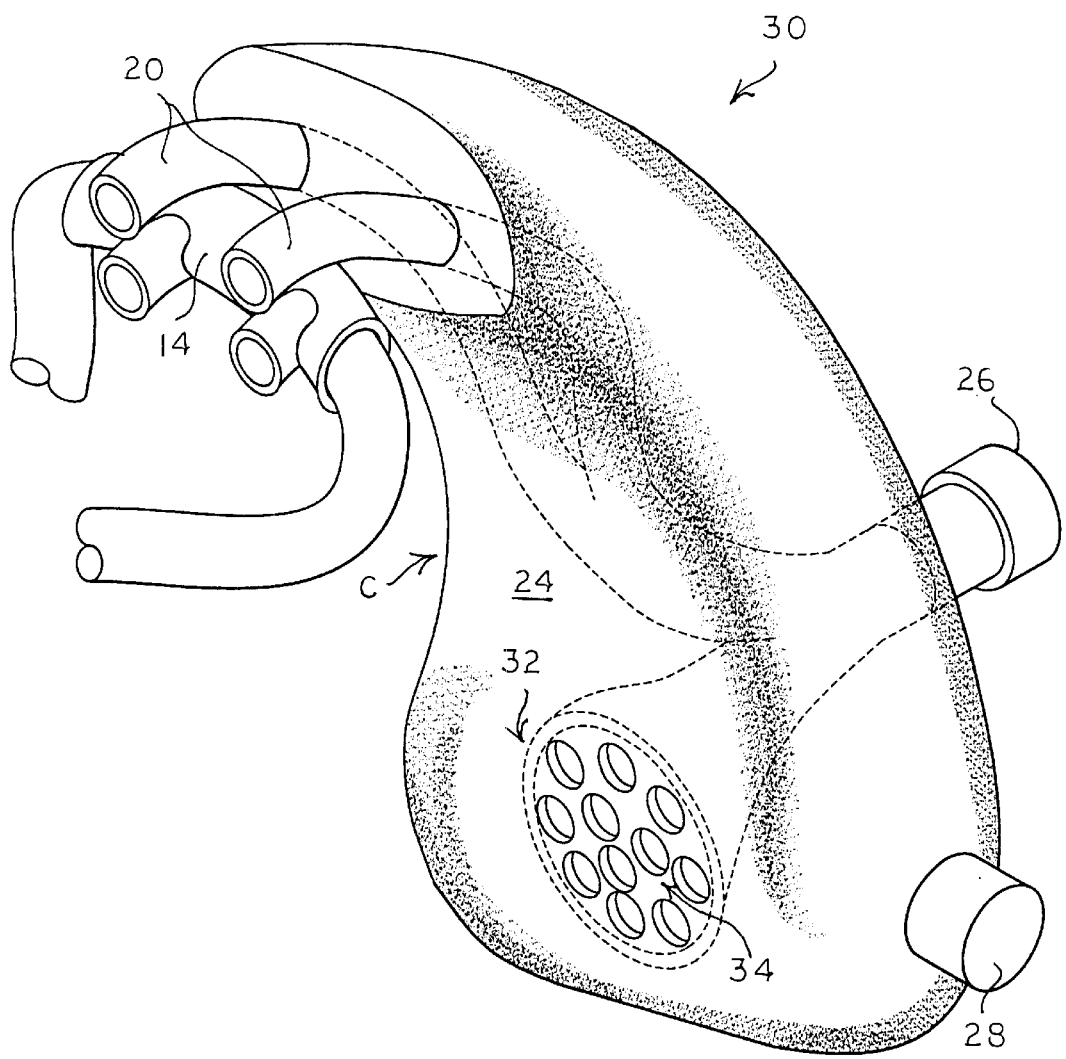
FIG. 3 is a perspective view similar to FIG. 2, but of a second embodiment of the end tidal carbon dioxide sampling device having an enlarged and apertured oral exhalation collection region.

As seen in FIG. 3, a second embodiment of the present invention modifies the end tidal sampling device 10 of FIGS. 1 and 2 to form a device 30 integrating a cannula 14 with the body 24. Device 30 has a flattened surface 32 with an array of apertures 34 which will collect the expired end tidal carbon dioxide gases from the mouth. This embodiment will be less intrusive to the patient.

The devices 10 and 30 can be made in a range of sizes to fit an adult down to an infant, and each device 10, 30 will have an appropriate curvature C.

The device is made of suitable plastics materials, known to those skilled in the art. The body and tubes may be made of similar or different plastics materials.

It is to be understood that the present invention is not limited to the embodiments described above, but encompasses any and all embodiments within the scope of the following claims.

I claim:

1. A respiratory carbon dioxide content measuring addition device for a cannula comprising:

an arcuate body, dimensioned and configured to conform to the configuration of a human face, and extending from the nostrils to the mouth;

said arcuate body containing a pair of nasal ducts having external flexible clips, a pair of oral ducts, and a collection and outlet duct;

said body is made of one plastic material, and said nasal ducts, oral ducts and outlet duct are made of a different plastics material;

whereby the device is attached by the clips to a cannula for collecting expired gases from a patient under sedation.

2. The respiratory carbon dioxide content measuring device according to claim 1, further comprising a pair of extensions proximate the oral ducts, for stabilizing the device relative to the patient's mouth.

3. The respiratory carbon dioxide content measuring device according to claim 1, wherein said nasal ducts and said oral ducts are combined to form a single said outlet duct.

4. A respiratory carbon dioxide content measuring device comprising:

a nasal cannula having two ducts;

an arcuate body integral with said cannula, dimensioned and configured to conform to the configuration of a human face, and extending from the nostrils to the mouth;

said arcuate body containing a pair of oral ducts, a collection and outlet duct, and a pair of extensions proximate the oral ducts, for stabilizing the device relative to the patient's mouth;

said body is made of one plastics material, and said nasal ducts, oral ducts and outlet duct are made of a different plastics material;

whereby the device collects expired gases from a patient under sedation.

5. The respiratory carbon dioxide content measuring device according to claim 4, wherein said nasal ducts and said oral ducts are combined to form a single said outlet duct.

6. A respiratory carbon dioxide content measuring device comprising:

a nasal cannula having two ducts;

an arcuate body integral with said cannula, dimensioned and configured to conform to the configuration of a human face, and extending from the nostrils to the mouth;

said arcuate body containing a flattened region, and said flattened region having an array of apertures for collecting exhaled oral gas, the body further including a collection and outlet duct;

said body is made of one plastics material, and said nasal ducts, array of apertures, and outlet duct are made of a different plastics material;

whereby the device collects expired gases from a patient under sedation.

7. The respiratory carbon dioxide content measuring device according to claim 6, further comprising a pair of extensions proximate the array of apertures, for stabilizing the device relative to the patient's mouth.

8. The respiratory carbon dioxide content measuring device according to claim 6, wherein said nasal ducts and said array of apertures are combined to form a single said outlet duct.

* * * * *